(12) United States Patent
Bonnet

(10) Patent No.: US 9,265,895 B2
(45) Date of Patent: Feb. 23, 2016

(54) PROTECTION DEVICE FOR A NEEDLE

(71) Applicant: Becton Dickinson France, Le Pont-de-Claix (FR)

(72) Inventor: Stephane Bonnet, Miribel Lanchatre (FR)

(73) Assignee: Becton Dickinson France S.A.S., Le Pont-de-Claix (FR)

( * ) Notice: Subject to any disclaimer, the term of this patent is extended or adjusted under 35 U.S.C. 154(b) by 0 days.

(21) Appl. No.: 14/164,643

(22) Filed: Jan. 27, 2014

(65) Prior Publication Data

US 2014/0142513 A1  May 22, 2014

Related U.S. Application Data

(63) Continuation of application No. 12/529,517, filed as application No. PCT/IB2008/002152 on Mar. 3, 2008, now Pat. No. 8,672,894.

(30) Foreign Application Priority Data

Mar. 2, 2007 (FR) ..................................... 07 01530

(51) Int. Cl.
*A61M 5/32* (2006.01)
*A61M 5/31* (2006.01)

(52) U.S. Cl.
CPC ..... *A61M 5/3202* (2013.01); *A61M 2005/3109* (2013.01)

(58) Field of Classification Search
CPC ............. A61M 2005/3109; A61M 2005/3118; A61M 5/3202

USPC .................. 604/181, 187, 192–198, 110, 201
See application file for complete search history.

(56) References Cited

U.S. PATENT DOCUMENTS

| | | | |
|---|---|---|---|
| 3,390,759 A | 7/1968 | Vanderbeck | |
| 5,858,008 A | 1/1999 | Capaccio | |
| 5,980,495 A | 11/1999 | Heinz et al. | |
| 6,551,286 B1 | 4/2003 | Claessens | |
| 2002/0062108 A1* | 5/2002 | Courteix | A61M 5/3202 604/198 |
| 2005/0038391 A1* | 2/2005 | Wittland | A61L 2/20 604/192 |

FOREIGN PATENT DOCUMENTS

| | | |
|---|---|---|
| EP | 1208861 A1 | 5/2002 |
| EP | 1690562 A1 | 8/2006 |
| JP | 10295814 A | 11/1998 |
| JP | 2005152541 A | 6/2005 |

* cited by examiner

*Primary Examiner* — Phillip Gray
(74) *Attorney, Agent, or Firm* — The Webb Law Firm

(57) ABSTRACT

The invention relates to a protection device for a needle of an assembly or of an injection device having a hub portion provided with a needle, the said protection device comprising: an outer casing formed of a first material; and an inner casing formed of a second material different from the said first material and defining a cavity for receiving in a sealing way at least the hub portion, said cavity having an inner wall; attachment means defined in the said cavity to removably engage and secure said protection device at least along a sealing line to the injection device; the protection device being characterized in that it further comprises aspiration limiting means for limiting the deformation of said cavity when said protection device is separated from the assembly or the injection device.

15 Claims, 12 Drawing Sheets

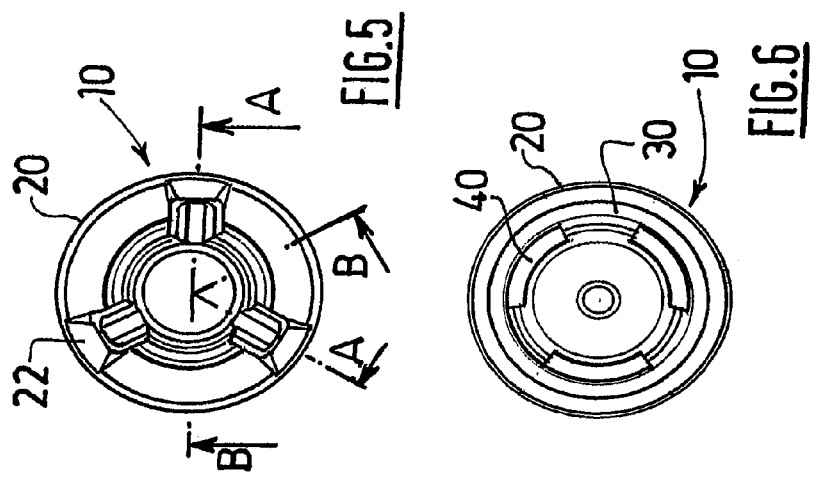
FIG.5
FIG.6
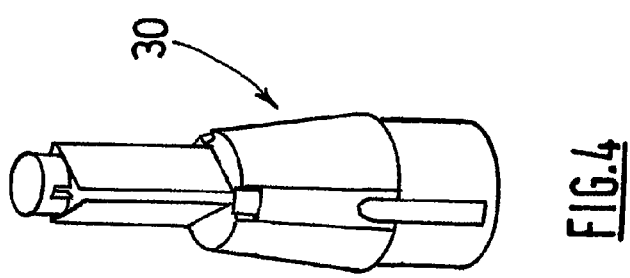
FIG.4
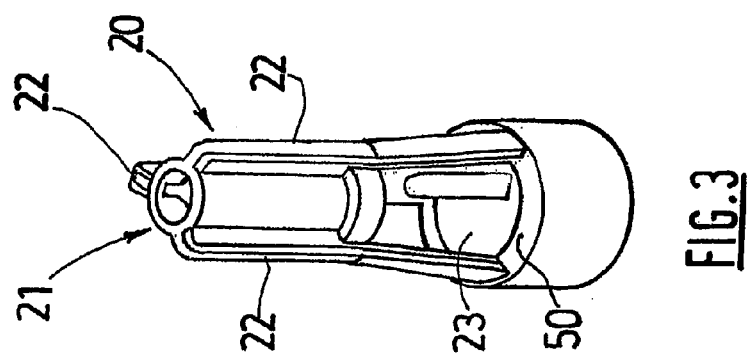
FIG.3

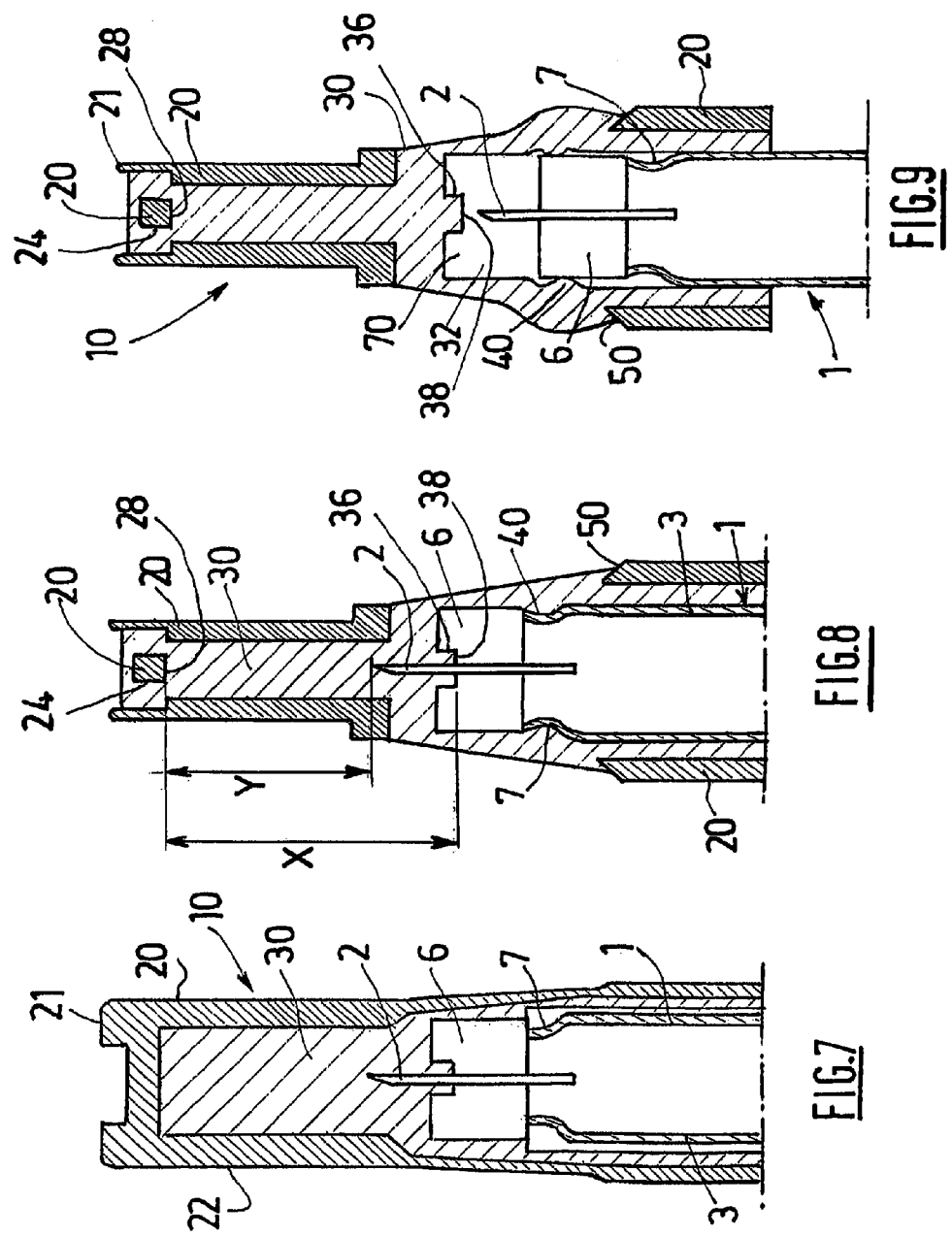

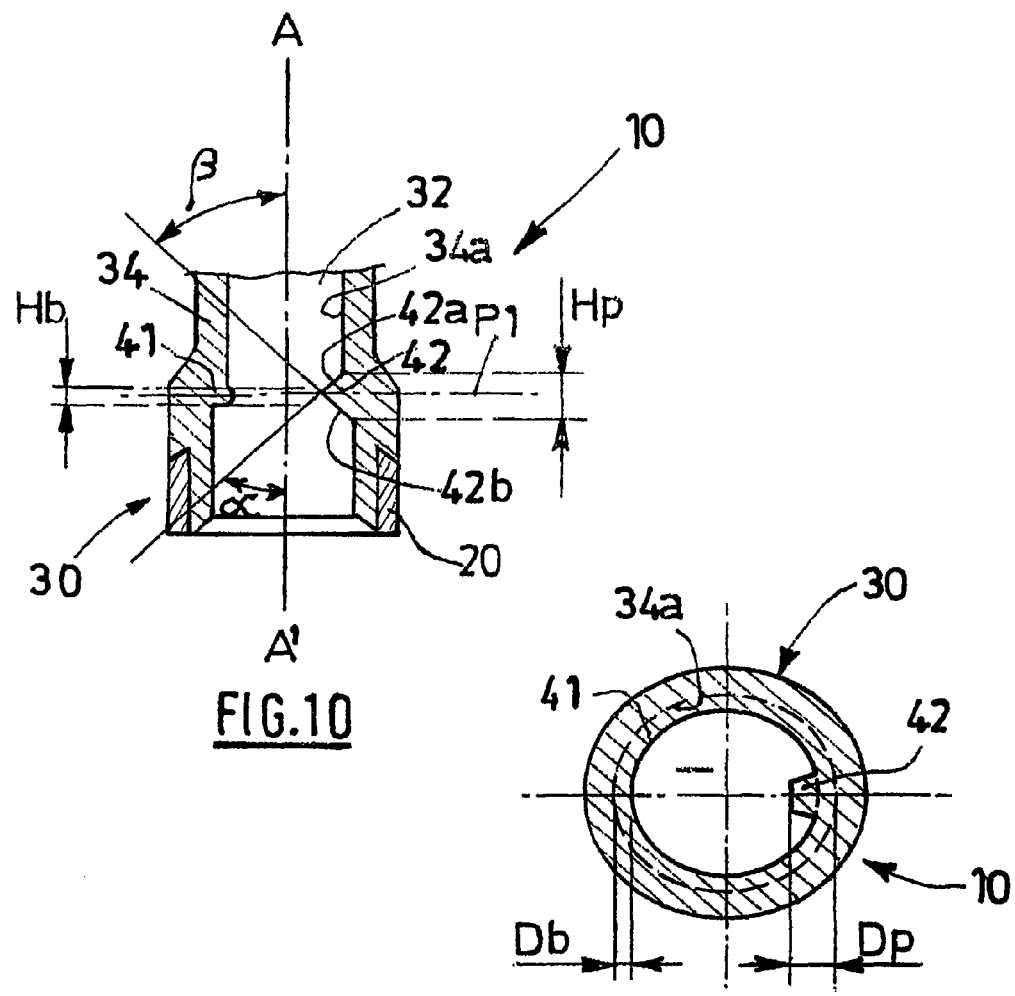

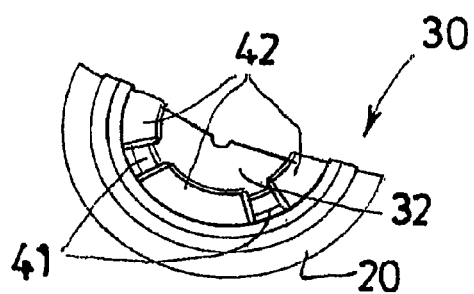
FIG.12C
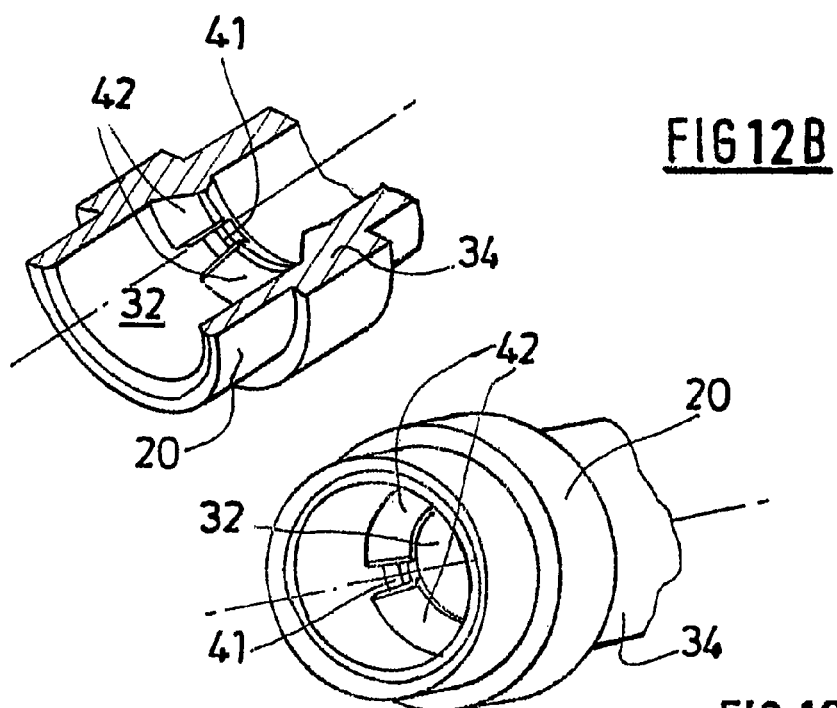
FIG.12B
FIG.12A

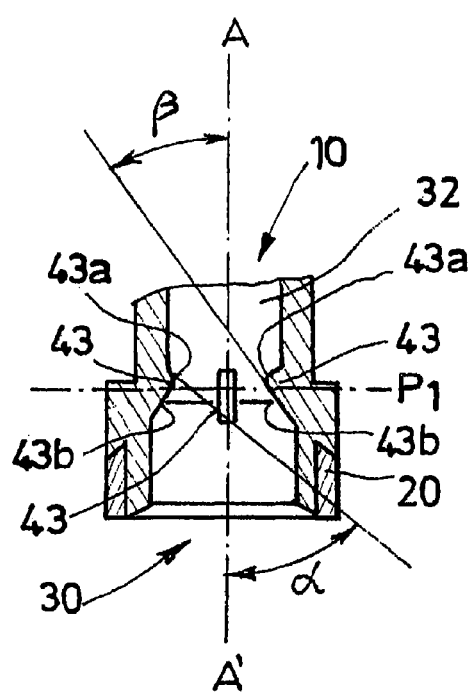
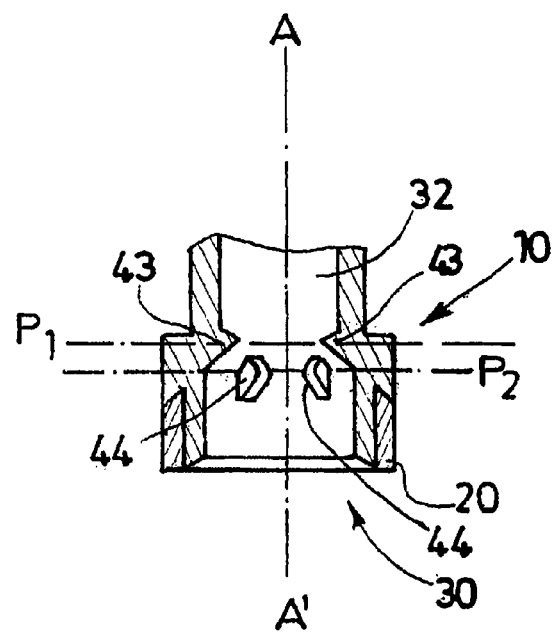
FIG. 16
FIG. 17

PROTECTION DEVICE FOR A NEEDLE

CROSS REFERENCE TO RELATED APPLICATIONS

This application is a continuation application of U.S. patent application Ser. No. 12/529,517 entitled "Protection Device for a Needle" filed Apr. 15, 2010, which is a U.S. National Stage application of PCT/IB2008/002152 entitled "Protection Device for a Needle" filed Mar. 3, 2008, which claims the benefit of French Application No. FR 07/01530, filed Mar. 2, 2007, the entire disclosures of each of which are hereby incorporated herein by reference.

The present invention relates to a protection device for a needle of an injection device or of an assembly.

In the present application, the distal end of a piece or a device is understood to be the end furthest from the hand of the user and the proximal end is understood to be the end closest to the hand of the user. Likewise, in the present application, "distal direction" is understood to be the direction of injection, and "proximal direction" is understood to be the direction opposite the direction of injection.

An injection device such as, for example, a syringe, must be handled with care before and after use due to the presence of a needle. To minimize the risk of accidental injury due to needle sticks, syringes are typically furnished on their hub with a needle shield that covers the sharpened tip of the needle. The needle shield is removed prior to use to expose the sharpened tip of the needle. Such a shield also serves to protect the sharpened tip of the needle and to preserve its sterility prior to use of the injection device.

It is known that, because of the seal present between the syringe hub and the needle shield, the removal of the needle shield from the syringe may cause an aspiration of a part of the medicinal liquid contained in the syringe through the needle, the said aspirated part being lost for the injection. In the case of injections of standard volumes of medication (i.e., in the milliliter range), such a phenomenon is of little importance, as the amount aspirated during the removal of the needle shield typically represents only a negligible amount of the complete dose of medicinal liquid to be injected.

However, in the case of intradermal injection, in which a short needle, typically in the range of 0.5 to 3.0 mm is provided on the syringe and in which a relatively small dose of liquid medicament is carried in the syringe and injected into the patient, aspiration of any of the liquid medicament means loss of a significant part of the intended dose amount. Precisely in the case of such intradermal injections, as for example in the case of vaccinations, it is particularly important to ensure stability of the dose that needs to be administered. Such aspiration may also prevent the reproducibility of the injections, as the dose amount may not be consistent due to aspiration of some of the liquid medicament.

Needle shields may have a generally pliable part and a generally rigid part. The generally pliable part allows to ensure a secure sealing connection with the syringe, at least along a sealing line, and the rigid part allows to provide a protection against accidental needle sticks and provides the user with an easily grippable surface for the user to remove the needle shield from the syringe.

There is therefore the need for a protection device such as a needle shield for a needle of an injection device or of a needle assembly, intended to be assembled on an injection device or on an assembly, said protection device limiting, even preventing, the aspiration of a part of the medicinal liquid when the said protection device is removed from the injection device prior to use of the injection device for completing an injection.

The present invention solves this problem by providing a protection device that limits the aspiration of medicinal liquid when the protection device is removed from the injection device or from the assembly. The inventive protection device is usable on an injection device having a staked needle (i.e., a needle that is non-removably secured to the syringe), or on an injection device having a removable needle such, as for example, a needle assembly attached via a Luer connection. In addition, the present invention is particularly useful for an injection device intended to deliver a small dose such as, for example, an intradermal injection.

The present invention is directed to a protection device, for a needle or for a needle assembly or for an injection device. The assembly or injection device has a hub portion defined at its distal end with a needle being provided thereat. The protection device comprises:

an outer casing formed of a first material;

an inner casing formed of a second material different from the said first material and defining a cavity for receiving in a sealing way at least part of the hub portion, said cavity having an inner wall;

attachment means defined in the said cavity to removably engage and secure said protection device to the assembly or injection device, along at least one sealing line; and aspiration limiting means designed for limiting the deformation of the cavity when said protection device is separated from the assembly or the injection device, the inventive protection device being characterized in that said attachment means comprise at least a first retainer defined on said inner wall and extending into said cavity and, a second retainer defined on said inner wall and extending into said cavity, said first retainer and second retainer being designed to, resiliently and releasably, engage a part of said assembly or injection device to secure said protection device thereto, said first retainer and second retainer having at least their shape or one of their dimensions different from the other, at least one of the first and second retainers being intended to define, with said hub portion, said sealing line.

The deformation of the cavity being thus limited upon withdrawal of the protection device, the sealing line formed by the pliable part moves simultaneously with the movement of the rigid part with respect to the hub. The fact that the sealing line does not remain still allows to limit the time during which the vacuum is created within the cavity and then to limit the risk of liquid aspiration. As will be described further, advantageously, the breaking of the contact between the sealing line and the hub occurs before the tip of the needle is withdrawn from the pliable part in which it is plugged in.

Indeed, when it is placed on the needle of an injection device or of an assembly, the protection device of the present invention seals the tip of the needle which penetrates the pliable part of the protection device. In a conventional syringe, when the needle shield is removed from the syringe, the sealing line tends to remain in place, the pliable part of the needle shield deforms and stretches. Because of the tightness which is present between the needle shield and the syringe hub, this deformation causes a vacuum in the cavity surrounding the needle. The formation of that vacuum causes aspiration of part of the liquid medicament which is contained in the barrel of the syringe. The present invention advantageously provides means for limiting aspiration that serves to limit in time the creation of the vacuum around the needle especially by ensuring that the generally rigid part and the generally pliable part of the needle shield move together as a user removes the needle shield from the syringe. Therefore, the sealing line is not operative anymore, and this before the tip of the needle is itself no more in sealing contact with the generally pliable part. That limits the time during which the vacuum is created in the cavity around the needle and thus limits aspiration of liquid medicament.

The protection device according to the invention is used to protect the needle of an injection device intended to inject low volume doses of medicinal liquid, without loss of the said liquid during removal of the protection device prior to use. In addition, the inventive protection device allows the reproducibility of the injection of low volume liquid doses.

In an embodiment of the present invention, the attachment means comprise at least a first bulge defined on the inner wall extending into the cavity and intended to define, with said hub portion, said sealing line.

In yet another embodiment of the present invention, the attachment means comprise a discontinuous annular abutment defined on the inner wall.

In an embodiment of the present invention, said aspiration limiting means comprise engaging means, designed for engaging said inner and outer casings one to the other and ensuring that said outer casing and said inner casing move together when said protection device is separated from the assembly or injection device.

In an embodiment of the present invention, the engaging means comprise a hook defined on the outer casing, and an abutment defined in the cavity. The hook engages the abutment to limit the relative movement of the sealing line with respect to the outer casing when the protection device is removed from the assembly or injection device. The hook can have, for example, a triangular shape or present an abutment surface perpendicular to the protection device axis.

Advantageously, with the protection device according to the invention, the time during which vacuum is created in the area of the sharpened tip of the needle by the distal movement of the protection device relative to the injection device is minimized, even suppressed. Specifically, due to the aspiration limiting means and attachment means, the sealing line between the needle shield and hub portion of the assembly or injection device is rapidly rendered ineffective when a user begins to remove the needle shield from the assembly or injection device.

In an embodiment of the present invention, said outer casing and said inner casing form a unitary part.

In a preferred embodiment of the invention, the outer casing and the inner casing are formed by one of a bi-material co-injection or a bi-injection process. The said first material is preferably more rigid than the said second material.

Preferably, the said first material may be polypropylene, or other materials having similar properties and characteristics. Such a material allows the said outer casing and the said inner casing to move together when the protection device is removed. For example, the said first material may be semi-rigid. In particular, thanks to the semi-rigid nature of the said outer casing, the said inner casing is pulled with the said outer casing when the user pulls on the distal gripping zone of the said outer casing and the whole of the protection device (i.e., both the outer and inner casings) moves in the distal direction relative to the injection device.

Preferably, the said second material is a pliable material such as Thermo Plastic Elastomer ("TPE").

Due to the deformable nature of the said second material, the inner casing is capable of deforming radially when the protection device is attached to or removed from the assembly or injection device, in particular when the hub portion of the assembly or injection device comes into contact with the annular abutment of the protection device.

In an embodiment of the invention, said outer casing has an interior abutment surface, and said inner casing has a needle plug defined in said cavity to receive substantially the tip of the needle when said hub portion is received in said cavity.

In an embodiment of the invention, said attachment means further comprise a second bulge, said second bulge having at least its shape or one of its dimension different from said first bulge, said second bulge further being circumferentially non-continuous about said interior cavity.

In an embodiment of the invention, the protection device of the invention comprises at least two first or second bulges, both being located in the same transversal plane.

In another embodiment of the invention, the protection device comprises at least two first or second bulges, both being located in different transversal planes.

Said first and/or second bulges may be regularly spaced from each other.

In an embodiment of the invention, at least one of said first or second bulge has a proximal face forming a predetermined angle $\beta$ with the longitudinal axis of said protection device, said predetermined angle $\beta$ ranging from 35° to 60°.

In an embodiment of the invention, at least one of said first or second bulge has a distal face forming a predetermined angle $\alpha$ with the longitudinal axis of said protection device, said predetermined angle $\alpha$ ranging from 20° to 40°.

In an embodiment of the invention, at least one of said first or second bulge has a cross-sectional shape of half a drop of water of which the widest part faces the distal end of said protection device.

In an embodiment of the invention, said first and/or second bulges define for said cavity a predetermined geometric shape, chosen in the group comprising a square, a triangle, an oblong format, a cross, and a star.

In an embodiment of the invention, said first retainer comprises at least a bead portion that extends radially into said interior cavity on a first predetermined distance Db, and said second retainer comprises at least a projection that extends radially into said interior cavity on a second predetermined distance Dp that is different than said first predetermined distance Db.

Said first retainer may comprise at least a bead portion that extends longitudinally in said interior cavity a first predetermined length Hb, and said second retainer may comprise at least a projection that extends longitudinally in said interior cavity a second predetermined length Hp that is different than said first predetermined length Hb.

In an embodiment of the invention, said first retainer or second retainer comprise a continuous annular bead.

Another aspect of the present invention is an assembly comprising a hub portion and a needle provided at said hub portion, said assembly being characterized in that it further comprises a protection device as described above.

In a preferred embodiment of the assembly, the tip of said needle is at a distance Y from said interior abutment surface when said needle is embedded in said needle plug, said distance Y being equal or superior to 0.5 mm.

Another aspect of the invention is a structure formed of an assembly and a protection device, the assembly comprising a hub portion and a needle provided at the hub portion, the protection device comprising at least a casing defining a cavity for receiving the hub portion and defining therewith at least a sealing line, the cavity defining a needle plug intended to receive, in a sealing way, the tip of the needle when the hub portion is received in the cavity, characterized in that the assembly and the protection device are designed such that, when the protection device is withdrawn from the assembly, the sealing line is rendered ineffective before the tightness between the tip of the needle and the needle plug is no more ensured.

Another aspect of the invention is an injection device comprising a hub portion and a needle provided at said hub portion, characterized in that it further comprises a protection device as described above.

According to an advantageous embodiment, the inventive injection device comprises a reservoir filled with a liquid product intended to be injected during an injection step, and is characterized in that, before the injection step, the reservoir comprises a volume less than 200 microliters of liquid product.

BRIEF DESCRIPTION OF DRAWINGS

Other advantages and variants of the present invention will be specified with the aid of the following description and the appended drawings in which:

FIG. 3 is a view in perspective of the outer casing of the protection device according to FIG. 2;

FIG. 4 is a view in perspective of the inner casing of the protection device according to FIG. 2;

FIG. 5 is a top view of the protection device according to FIG. 2 in total;

FIG. 6 is a bottom view of the protection device according to FIG. 2 in total;

FIG. 7 is a cross-sectional view along the line A-A of FIG. 5 of the protection device of the invention when assembled on an injection device;

FIG. 8 is a cross-sectional view along the line B-B of FIG. 5 of the protection device of the invention when assembled on an injection device;

FIG. 9 is a cross-sectional view of the protection device according to FIG. 8 when the protection device has been partially removed from the injection device;

FIG. 10 is a cross-sectional view of an alternative embodiment of the inner casing of the protection device of the invention;

FIG. 11 is a bottom view from the proximal end of the inner casing of the protection device of FIG. 10;

FIGS. 12A, 12B, and 12C are respectively a perspective view, a perspective cross-sectional view according to the longitudinal axis, and half of a bottom view of an alternative of the inner casing of the protection device of FIG. 10;

FIG. 16 is a cross-sectional view of another alternative embodiment of the inner casing of the protection device according to the invention;

FIG. 17 is a cross-sectional view of another alternative embodiment of the inner casing of the protection device according to the invention;

DESCRIPTION OF THE PREFERRED EMBODIMENTS

Figure 1:
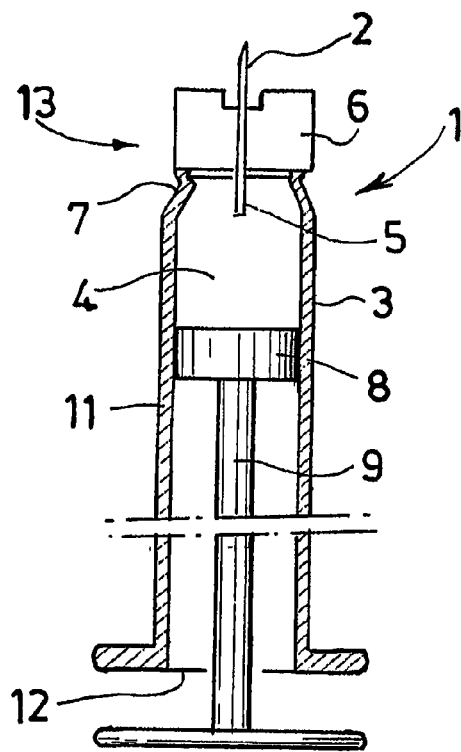
FIG. 1 is a view in section of an injection device furnished with a needle intended to receive a protection device according to the invention.

FIG. 1 shows an injection device 1 such as a syringe, for example, furnished with a needle 2 and sized and shaped for receiving a protection device according to the invention. In the example shown in FIG. 1, the needle 2 is short, preferably in the range of 0.5 mm to 3 mm. Such a needle length may be used to perform an injection into the dermis layer of the skin also referred to as an intradermal injection.

The injection device 1 of FIG. 1 has an open proximal end 12 and a substantially closed distal end 13 and a sidewall 11 extending therebetween defining a reservoir 3 of the injection device 1. The reservoir 3 is sized and shaped to contain a liquid medicament in the injection device 1. The injection device 1 also includes, at its distal end, a neck portion 7 which narrows with respect to the reservoir 3. The injection device 1 also includes, at its distal end a hub portion 6 which is sized and shaped to accept the needle 2 that extends into and is in communication with the reservoir 3. The needle 2 thus defines a path 5 through which the liquid medicament 4 may flow from the reservoir 3 to be injected into the injection site, for example the skin of a patient.

The injection device or syringe 1 shown in FIG. 1 also includes a plunger rod 9 having a plunger 8 provided at an end thereof. The plunger 8 is caused to slidably move in the reservoir 3 along an inner surface of the sidewall 11 to cause the liquid medicament 4 to be expelled from the reservoir 3 through the needle 2.

Figure 2:
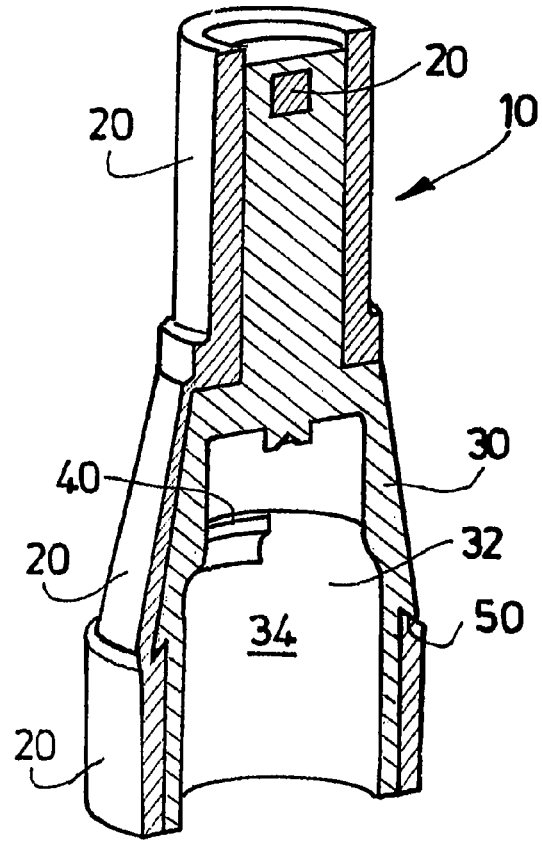
FIG. 2 is a cross-sectional perspective view of half of a protection device according to the invention.

FIG. 2 shows a protection device 10 according to an embodiment of the present invention. The inventive protection device 10 comprises an outer casing 20 and an inner casing 30 preferably formed using a bi-material co-injection process, or a bi-injection process. The outer casing 20 is made of a material that is more rigid than the material from which the inner casing 30 is made. Preferably, the outer casing 20 is made of polypropylene and the inner casing 30 is made of a deformable material such as TPE (Thermo Plastic Elastomer).

FIGS. 3 and 4 respectively show, separated for greater clarity, the outer casing 20 and the inner casing 30.

With reference to FIG. 2, the inner casing 30 has an inner wall 34 that defines a cavity 32 sized and shaped to receive the hub portion 6 of the injection device 1, as will be explained hereinafter.

On the inner wall 34 of the cavity 32 at least one bulge in the form of a discontinuous annular abutment 40 is defined. The annular abutment 40 provides means for removably attaching the inventive protection device 10 to an injection device 1. Alternatively, the annular abutment 40 may be continuous.

Moreover, the inner wall 34 is able to resiliently deform around the hub portion 6 so as to form a sealing zone, at least a sealing line.

With reference to FIG. 3, the outer casing 20 comprises a distal gripping zone 21 by which the user can grasp the said protection device 10, for example in order to remove it from the injection device 1 to which it is attached. In the example shown in FIG. 3, this gripping zone comprises three ridges 22 to improve the user's grip. The outer casing 20 also comprises three windows 23. As will be explained hereinafter, these windows 23 are intended to allow the inner 30 casing to deform radially when the protection device 10 is removed.

With reference again to FIG. 2, the outer casing 20 also comprises a hook 50 in the form of an annular bevel of triangular shape on the example shown. The hook 50 can have other shapes, for example, it can present an abutment surface perpendicular to the protection device 10 axis. This hook 50 interacts with the inner casing 30 in order to cause the inner casing 30 and outer casing 20 to move together, i.e., as a unitary part, when the protection device 10 is removed from the injection device 1. Thus, when a user grips the outer casing 20 when removing the protection device 10 from the injection device 1, the outer casing 20 and inner casing 30 move together, in a substantially unitary manner without the sealing line remaining still. In that way, elongation or deformation of the inner casing 30 along its longitudinal direction is minimized. The hook 50 functions as retention means ensuring that the outer casing 20 and inner casing 30 are retained in a substantially unitary manner, as just described.

FIGS. 5 and 6 are top and bottom views, respectively, of the inner casing 30 of the inventing protection device 10. FIGS. 7 and 8 show the protection device 10 according to the present invention mounted on an injection device 1. In FIG. 7, the protection device 10 is shown in cross-section taken along the line A-A of FIG. 5, while FIG. 8 is a cross-section taken along the line B-B of FIG. 5. As shown in FIGS. 7 and 8, the protection device 10 removably fits over the distal end of the injection device 1 so that the needle 2, hub portion 6, and neck portion 7 are contained within the cavity 32. Preferably, the annular abutment 40 rests, at least partly, in or near the neck portion 7. The distal tip (i.e., the sharpened tip) of the needle 2 is preferably contained within the inner casing 30 such that the sharpness and sterility of the sharpened tip is maintained. In addition, the sharpened point of the needle 2 is safely secured and shielded by the inventive protection device 10 so that accidental needle stick injury is prevented.

As shown on FIGS. 8 and 9, the outer casing 20 has an interior abutment surface 24 having a proximally facing surface 28 and the inner casing 30 has a needle plug 36 defined in the cavity 32 and in which it is embedded. The needle plug 36 has a proximally facing surface 38 located a distance X from the proximally facing surface 28 of the interior abutment surface 24, as shown on FIG. 8: this distance X is sufficient to receive substantially the tip of the needle 2 when the hub portion 6 of the injection device 1 is received in the cavity 32 and to ensure that the tip of the needle 2 is at a distance Y from the proximally facing surface 28 of the abutment surface 24. In the example of FIGS. 7-9, this distances X and Y are, for example, each above 5 mm.

Prior to use of the injection device 1, the user must remove the inventive protection device 10 to expose the sharpened tip of the needle 2 and open the path 5 defined by the needle 2 thereby permitting the liquid medicament to be caused to flow from the reservoir 3. Preferably, the user grips the outer casing 20 by or near the distal gripping zone 21 and pulls on the said outer casing 20 in the distal direction. As described above, the hook 50 ensures a generally unitary relationship between the inner casing 30 and outer casing 20 so that both parts essentially move as one piece as the inventive protection device 10 is removed from the injection device 1. Again, the hook 50 retains the generally unitary relationship between the outer casing 20 and inner casing 30 to reduce any stretching between those parts and cause the movement of the sealing line. Due to the relatively small amount of liquid medicament provided in the reservoir 3 for an intradermal injection, it is highly desirable to minimize the elongation of the inner casing 30 as the inventive protection device 10 is removed from the injection device 1 and thereby limit aspiration of liquid medicament from the reservoir 3 as the protection device 10 is removed from the injection device 1.

During removal of the protection device 10, the hub portion 6 of the injection device 1 comes into contact with the discontinuous annular abutment 40, which deforms thereby causing the radial outward deformation of the inner casing 30. This radial deformation is depicted generally in FIG. 9, and is further facilitated by the windows 23 defined in the outer casing 20 (see, e.g., FIG. 3).

Such removal of the protection device 10 from the injection device 1 may create a vacuum in the space 70 created by the movement of the protection device 10 in a distal direction off of the injection device 1. That vacuum may also cause liquid medicament to be drawn from the reservoir 3 and through the needle 2. To prevent this undesired effect, the present invention advantageously provides a discontinuous annular abutment 40, which serves to immediately break the vacuum. Thus, any aspiration created by removal of the protection device 10 is not sufficient to cause any significant amount of the liquid medicament to be drawn through the needle 2. In this view, it is advantageous to size the protection device 10 and the injection device 1 so that, when the protection device is removed from the injection device 1, the sealing line is rendered ineffective before the tightness between the tip of the needle 2 and the needle plug 36 is no more ensured.

In reference to FIGS. 10 and 11, is shown an alternate embodiment of an inner casing 30 of the protection device 10 of the invention. The references pertaining to the same elements as in FIGS. 1-9 have been preserved.

The inner casing 30 of FIG. 10 comprises a first retainer forming an annular bead portion 41 defined on the wall 34 and extending from the internal face 34a of said wall 34 into the cavity 32. The annular bead portion 41 may be continuous around the whole said cavity 32 (see FIG. 11).

The inner casing 30 also comprises a second retainer forming a projection 42 extending from the annular bead portion 41 into the cavity 32. As is shown on FIG. 10, the annular bead 41 and the projection 42 are located in the same transversal plane P1.

FIG. 11 is a cross section view of the inner casing 30 of FIG. 10 along the transversal plane P1 of FIG. 10: on FIG. 11 the internal face 34a of the wall 34 is shown in dashes. As appears clearly on this Figure, the annular bead portion 41 extends radially from said internal face 34a into said cavity 32 on a first predetermined distance Db, and said projection 42 extends radially from said internal face 34a into said interior cavity 32 on a second predetermined distance Dp that is greater than said first predetermined distance Db.

Moreover, as appears from FIG. 10, the annular bead portion 41 extends longitudinally into said cavity 32 on a first predetermined length Hb, and said projection 42 extends longitudinally into said cavity 32 on a second predetermined length Hp that is greater than said first predetermined length.

As shown on FIG. 10, the projection 42 has a distal face 42a that forms an angle α with the longitudinal axis AA' of the inner casing 30, and a proximal face 42b that forms an angle β with said longitudinal axis AA'. The angle α preferably ranges from 20 to 40°. On the example shown, the angle α has a value of 30°. The angle β preferably ranges from 35 to 60°. On the example shown, the angle β has a value of 45°.

In alternate embodiments of the invention, the inner casing 30 may comprise one or more additional annular beads and/or projections, in addition to the first annular bead 41 and to the first projection 42 as described in reference with FIG. 10. The additional annular beads and/or projections may be identical or different in shape or in dimension from said first annular bead 41 and first projection 42 respectively. They may be located in the same transversal plane as the first annular bead 41 and/or projection 42 or on the contrary in different transversal planes.

FIGS. 12A to 14C are illustrative views of such alternative embodiments comprising additional projections. The references designating the same elements as in FIG. 10 have been maintained on all these Figures.

On FIGS. 12A to 12C is shown an alternative embodiment of the inner casing of FIG. 10 comprising a plurality of projections 42 regularly spaced from each other. In the example shown, the inner casing 30 comprises one annular bead 41 and four (partially shown) projections 42, located in the same transversal plane as the annular bead 41.

Figure 13C:
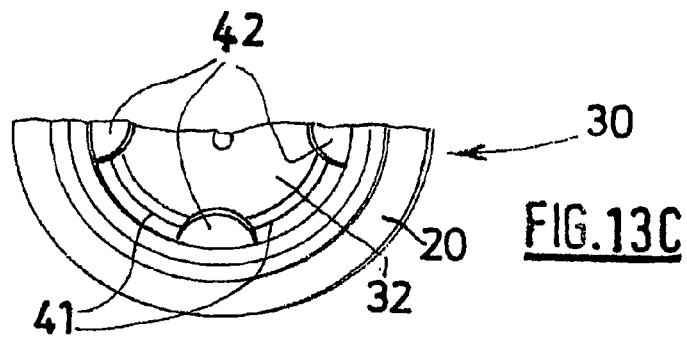
FIGS. 13A, 13B, and 13C are respectively a perspective view, a perspective cross-sectional view according to the longitudinal axis, and half of a bottom view of an alternative of the inner casing of the protection device of FIG. 10.
Figure 13B:
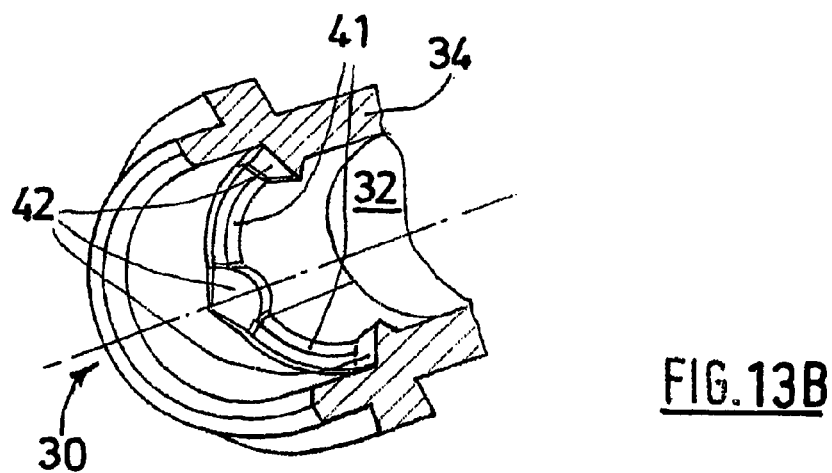
Figure 13A:
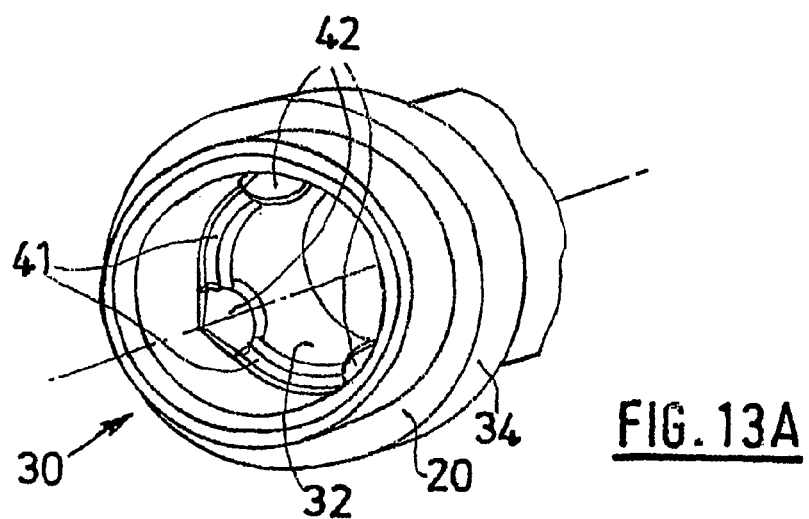

On FIGS. 13A to 13C is shown an alternative embodiment of the inner casing 30 of FIG. 10 comprising a plurality of projections 42 regularly spaced from each other. In the example shown, the inner casing 30 comprises one annular bead 41 and four (partially shown) projections 42, located in the same transversal plane as the annular bead 41. The projections 42 of the inner casing 30 of FIGS. 13A to 13C have the shape of half a drop of water, the widest part of said drop of water facing the distal end 30b of the inner casing 30.

Figure 14C:
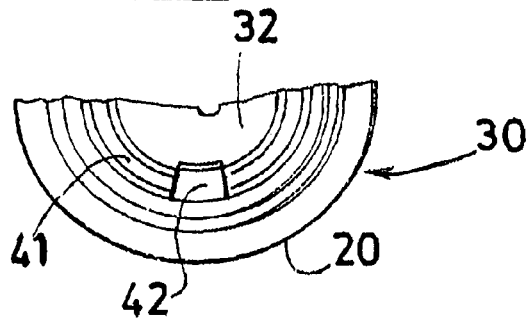
FIGS. 14A, 14B, and 14C are respectively a perspective view, a perspective cross-sectional view according to the longitudinal axis of a perspective view, and half of a bottom view of an alternative of the inner casing of the protection device of FIG. 10.
Figure 14B:
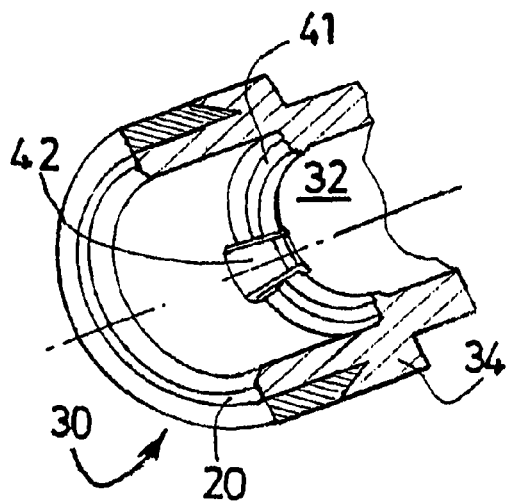
Figure 14A:
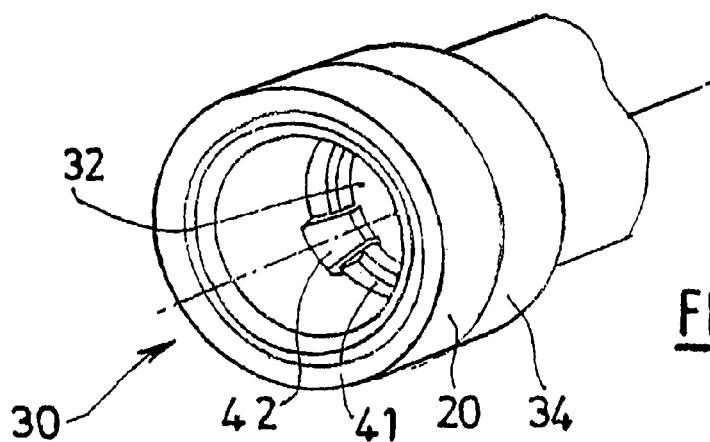

On FIGS. 14A to 14C is shown an alternative embodiment of the inner casing 30 of FIG. 10 comprising at least one projection 42 and at least one annular bead 41.

Depending on the respective shape and number of annular beads and/or projections, said annular beads and/or projections may define for the cavity 32 a shape chosen in the group comprising a square, a triangle, an oblong format, a cross, a star, or other geometric shapes suitable to provide the desired functionality and characteristics.

The first annular bead 41, the first projection 42 and the optionally additional annular beads and/or projections are designed to be able to, resiliently and releasably, engage a part of an injection device to secure the protection device 10 thereto.

Figure 15A:
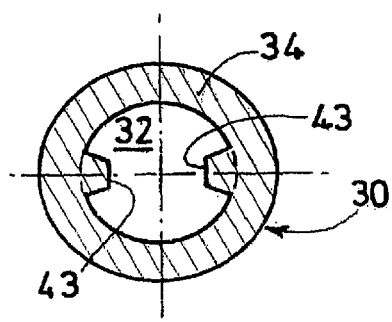
FIGS. 15A to 15D are cross section views similar to FIG. 11 for alternative embodiments of the inner casing of the protection device according to the invention.

FIG. 15A is a cross section view similar to FIG. 11 for an alternative embodiment of the inner casing of the protection device of the invention, in the case where said protection device comprises at least one first bulge 43. The embodiment of FIG. 15A comprises two first bulges 43. As appears from this Figure, the two first bulges 43 are diametrically opposed, though other arrangements are also contemplated by and within the scope and spirit of the present invention.

Figure 15B:
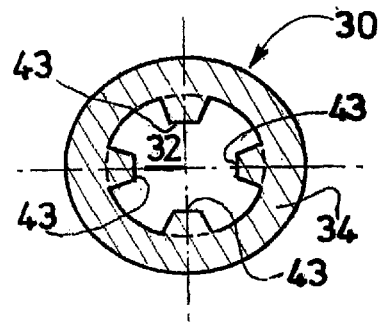

On FIG. 16 is shown another alternative embodiment of the inner casing 30 of the protection device 10 of the invention wherein the inner casing 30 comprises four identical first bulges 43 (among which only three are visible on the Figure), defined on the internal face of the wall 34, said first bulges 43 extending into the interior cavity 32. The references designating the same elements as in FIG. 10 have been maintained on FIG. 16. As appears more clearly from FIG. 15B, which is a cross section view of the inner casing 30 of FIG. 16 along the transversal plane P1, the first bulges 43 are located in the same transversal plane P1, regularly spaced and having the shape of half a drop of water. The widest part of the half drop of water faces the distal end 30b of the inner casing 30. Because of this specific shape of the first bulges 43, the distal face 43a of the first bulges 43 form an angle α of approximately 30° with the longitudinal axis of the inner casing 30, and the proximal face 43b of the first bulges 43 form an angle β of approximately 45° with the longitudinal axis of the inner casing 30. The installation and the removal of the protection device 10 on a needle hub (not shown) are therefore facilitated.

Figure 15C:
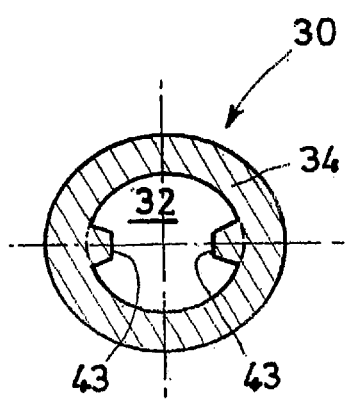
Figure 15D:
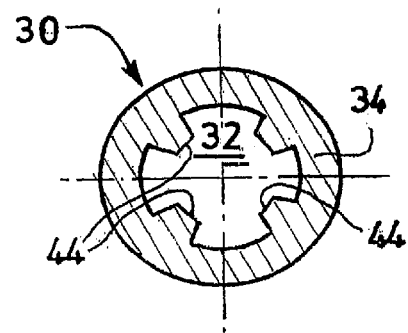

On FIG. 17 is shown a further alternative embodiment of the inner casing 30 of FIG. 16 which comprises two first bulges 43 and four second bulges 44 defined on the internal face of the wall 34, said first and second bulges 43, 44 extending into the interior cavity 32. The first and second bulges 43, 44 are designed to be able to, resiliently and releasably, engage a part of a needle assembly (not shown) to secure the protection device 10 thereto. The references designating the same elements as in FIG. 16 have been maintained on FIG. 17. As appears more clearly from FIG. 15C, which is a cross section view of the inner casing 30 of FIG. 17 along the transversal plane P1, the first bulges 43 are located in a first transversal plane P1 and diametrically opposed one to the other and form circumferentially non-continuous projections. As appears more clearly from FIG. 15D, which is a cross section view of the inner casing 30 of FIG. 17 along the transversal plane P2, the second bulges 44 are located in the same second transversal plane P2 and regularly spaced. Such an arrangement of first and second bulges 43, 44, on different transversal planes P1, P2 allows to better maintain the inner casing 30 on the needle assembly with a more uniformed maintaining force distributed on a larger portion of the needle hub 6 and without increasing the force required for the removal of the protection device 10.

Figure 18A:
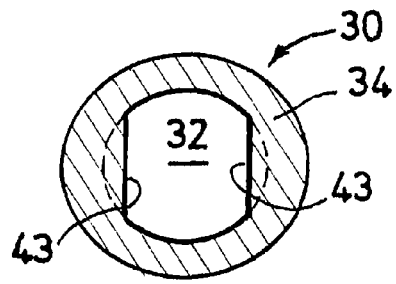
FIGS. 18A to 18H are cross-sectional views similar to FIGS. 15A-D for alternative embodiments of the inner casing of the protection device according to the invention.
Figure 18B:
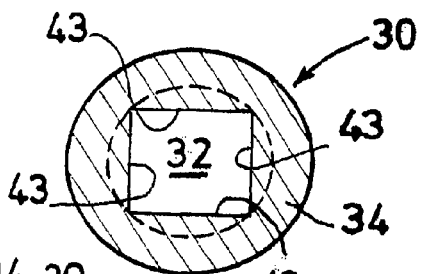
Figure 18C:
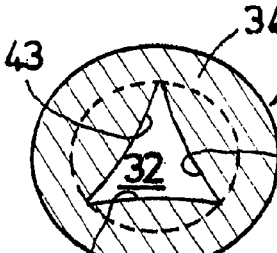
Figure 18D:
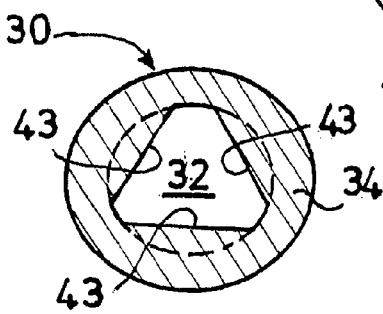
Figure 18E:
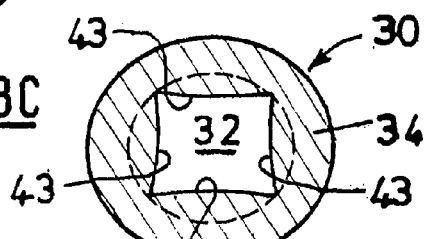
Figure 18F:
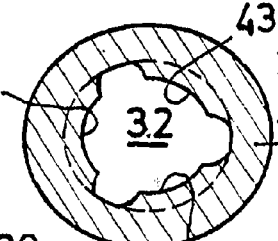
Figure 18G:
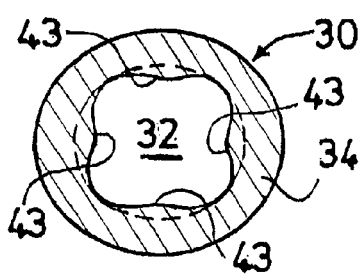
Figure 18H:
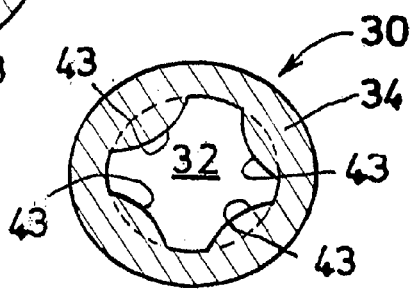
Figure 20:
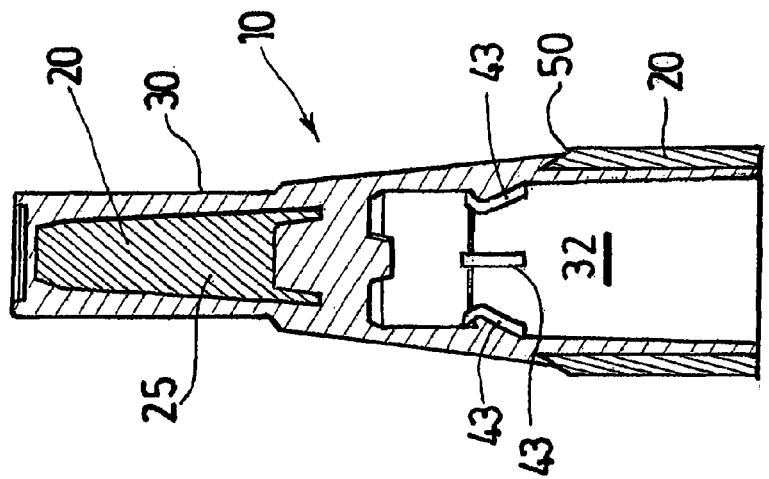
FIG. 20 is a cross-sectional view along the line B-B of FIG. 5 for the alternative embodiment of the invention of FIG. 19.
Figure 19:
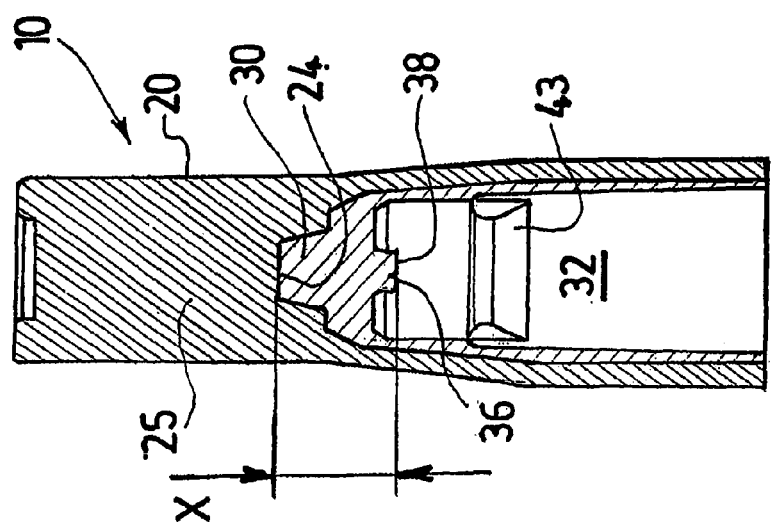
FIG. 19 is a cross-sectional view along the line A-A of FIG. 5 for an alternative embodiment of the invention.
Figure 22:
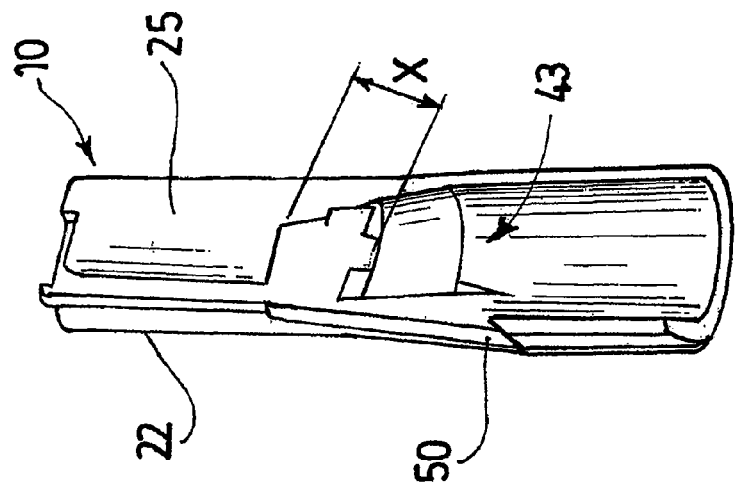
FIG. 22 is a cross-sectional perspective view of the protection device of FIGS. 19-20.
Figure 21:
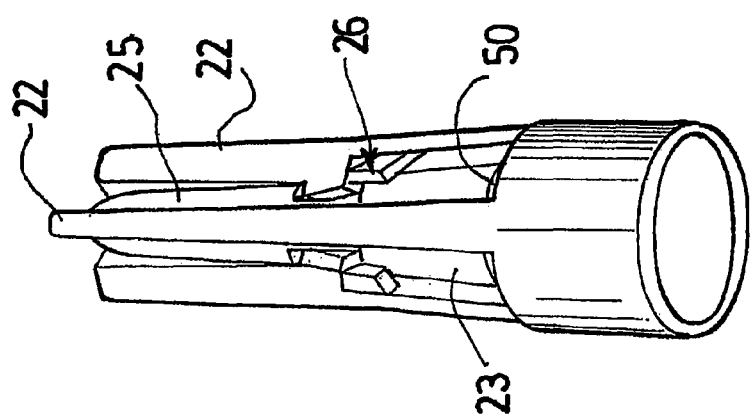
FIG. 21 is a perspective view of the outer casing of the embodiment of FIGS. 19-20.

On FIGS. 18A to 18H are shown cross section views similar to FIGS. 15A-D for alternative embodiments of the inner casing 30 of the protection device 10 of the invention where the first bulges 43 define a predetermined geometric shape. In particular:

in FIG. 18A, the first bulges 43 define an opening for the cavity 32 a shape of an oblong format,
  in FIGS. 18B, 18E, and 18G, the first bulges 43 define an opening for the cavity 32 a shape similar to or substantially similar to a square,
  in FIGS. 18C and 18D, the first bulges 43 define an opening for the cavity 32 a shape substantially similar to a triangle,
  in FIG. 18F, the first bulges 43 define an opening for the cavity 32 a shape substantially similar to a star,
  in FIG. 18H, the first bulges 43 define an opening for the cavity 32 a shape substantially similar to a cross.

The second bulges 44 can also define one of the predetermined geometric shape described above.

On FIGS. 19-22 is shown another embodiment of the protection device 10 of the invention, in which the outer casing 20 comprises an inner core 25 and relief structures 26 at the proximal end of said core 25. The references relating to the same elements as in FIGS. 1-9 have been preserved. The inner core 25 provides an abutment surface 24 for the material of the inner casing 30 near the needle plug 36. As shown on FIGS. 19 and 22, the needle plug 36 has a proximally facing surface 38 located a distance X from the abutment surface 24. The distance X is sufficient to cover the tip of the needle (not shown) without any contact between the tip of the needle and the abutment surface 24, but limited in order to reduce the compression of the inner casing material at the time the protection device 10 is assembled on the needle assembly. This improves the precision and reliability of the needle embodiment in the needle plug 36. Moreover, the distance X also reduces the amount of material needed at the needle plug 36, thus reducing the risk of sinking at moulding. In this example, the distance X is of few millimeters in order to leave a distance Y (not shown) between the abutment surface 24 and the tip of the needle of at least 0.5 mm.

The relief structures 26 provided at the proximal end of the inner 25 (see FIG. 21) advantageously serve to prevent the ridges 22 from collapsing during the injection of the material of the inner casing. The protection device 10 of FIGS. 19-22 may be manufactured by co-injection without transfer of the outer casing 20 and the inner casing 30. Alternatively, the protection device 10 of FIGS. 19-22 may be manufactured by bi-injection with transfer of the outer casing 20 and the inner casing 30. The presence of the relief structures 26 also reduces the amount of material of the inner casing inside the cavity and therefore contributes to improve the dimensional stability of the cavity.

The protection device according to the present invention, as herein described, depicted and claimed, thus makes it possible to protect the sharpness and ensure the sterility of the needle of an assembly or of an injection device intended for the injection of very low volume doses of liquid medicament (i.e., for intradermal injection). The inventive protection device makes the forgoing possible without risking the loss of a significant part of the said dose of liquid medicament when the protection device is removed from the injection device prior to use.

It will be obvious to a person skilled in the art from the disclosure provided herein that certain substitutions and variations made be made with respect to various parts of the present without departing from the scope and spirit of the present invention. For example, although a syringe is provided as one example of an injection device, the present invention clearly contemplates any injection device now known or hereafter developed having a needle secured or securable thereto and useful for injecting a medicament into a patient.

What is claimed is:

1. A protection device for a needle of a needle assembly, the needle assembly including a hub portion for holding the needle, the protection device comprising:
    an outer casing having at least one window opening;
    an inner casing engaged with the outer casing, the inner casing having an inner wall defining a cavity configured to receive at least the hub portion; and
    at least one protrusion extending from the inner wall of the inner casing for removably securing the inner casing to the needle assembly, the at least one protrusion cooperating with the needle assembly to form at least one sealing line, wherein at least a portion of the at least one protrusion is aligned with the at least one window opening in the outer casing and upon removal of the protection device from the needle assembly, the hub portion contacts the at least one protrusion and radially deforms the inner casing in an area adjacent the at least one window opening, and
    wherein the inner casing is fixedly engaged with the outer casing such that the inner casing and the outer casing function as a unitary member, limiting deformation of the cavity, along a longitudinal direction of the inner casing.

2. The protection device of claim 1, wherein upon removal of the protection device, the at least one sealing line moves simultaneously with the movement of the protection device, limiting the time a vacuum is created within the cavity.

3. The protection device of claim 1, wherein the at least one protrusion comprises a discontinuous annular abutment which cooperates with the hub portion to break a vacuum created within the cavity during removal of the protection device.

4. The protection device of claim 1, wherein the at least one protrusion comprises a continuous annular abutment.

5. The protection device of claim 1, wherein the at least one protrusion comprises at least a first retainer and a second retainer.

6. The protection device of claim 1, wherein the inner casing and the outer casing include cooperating abutment members for fixedly engaging one another.

7. The protection device of claim 6, wherein the outer casing comprises a hook and the inner casing comprises an abutment surface configured to engage the hook to ensure that the outer casing and the inner casing move as a unitary member upon removal of the protection device from the needle.

8. The protection device of claim 1, wherein the outer casing is formed from a first material and the inner casing is formed from a second material and wherein the first material is more rigid than the second material.

9. The protection device of claim 8, including a plurality of windows in the outer casing wherein the plurality of windows allow a portion of the inner casing to radially deform in an outward direction during removal of the protection device.

10. The protection device of claim 1, wherein the outer casing includes a plurality of ridges for gripping the protection device.

11. The protection device of claim 1, wherein the needle includes a distal tip that is contained within the inner casing.

12. The protection device of claim 11, wherein the inner casing includes a needle plug for receiving the distal tip of the needle when the hub portion is received in said cavity.

13. The protection device of claim 12, wherein the outer casing includes an interior abutment surface and wherein the distal tip of the needle is located a distance Y from the interior abutment surface when the distal tip of the needle is embedded within the needle plug wherein the distance Y is greater than or equal to 0.5 mm.

14. The protection device of claim 1, wherein the at least one protrusion comprises at least a first bulge and a second bulge, wherein the first bulge and the second bulge have at least their shape or one of their dimensions different from the other.

15. The protection device of claim 14, wherein the first and second bulges are located in different transversal planes.

* * * * *